United States Patent [19]

Clemmensen et al.

[11] Patent Number: 4,853,220
[45] Date of Patent: Aug. 1, 1989

[54] PROTEIN ISOLATED FROM BLOOD, PROCESS FOR PREPARING SAID PROTEIN, AANTIBODIES AGAINST SAID NEW PROTEIN, AND PHARMACEUTICAL COMPOSITIONS CONTAINING SAID PROTEIN OR SAID ANTIBODIES

[75] Inventors: Inge D. Clemmensen, Farum, Denmark; Cornelis Kluft, Sassenheim, Netherlands

[73] Assignee: Nederlandse Centrale Organisatie Voor Toegerastnatuurwete Nschappelijk Onderzoek, The Hague, Netherlands

[21] Appl. No.: 872,613

[22] Filed: Jun. 10, 1986

[30] Foreign Application Priority Data

Jun. 11, 1985 [NL] Netherlands ......................... 8501682

[51] Int. Cl.$^4$ ..................... A61K 37/02; C07K 13/00; C07K 15/06; C07K 15/12
[52] U.S. Cl. ...................................... 424/101; 514/12; 514/21; 530/350; 530/380; 530/829; 530/830; 530/413; 530/387; 424/85.8
[58] Field of Search ............... 530/350, 380, 829, 830, 530/387, 413; 514/12, 21; 424/101, 85

[56] References Cited

U.S. PATENT DOCUMENTS 4,499,014  2/1985  Estis ..................................... 530/829

OTHER PUBLICATIONS

Clemmensen et al., Eur. J. Biochem. 156, pp. 327-333 (4/15/86).
Clemmensen et al, Xth International Congress on Thrombosis and Haemostasis, No. 1, vol. 54, p. 877 (7/14/85).
Kluft et al, Xth International Congress on Thrombosis and Haemostasis, No. 1, vol. 54, p. 878 (7/14/85).
R. J. Owens et al, "Cellular Distribution of p68, a New Calcium-Binding Protein from Lymphocytes", Bioligical Abstracts, vol. 78, 1984.
Eur. J. Biochem. 120, 105-112 (1981).
Biochim. Biophys. Acta 668, 377-387 (1981).
Christensen, U. and Clemmense, I. (1978) Biochem. J. 175, 635.641.
"Progress in Chemical Fibrinolysis and Thrombolysis", (Davidson, J. F., Rowan, R. M., Samana, M. M. and Desnoyers, P. C. eds.) vol. 3, pp. 191-209, Raven Press, New York (1978).
J. Biol. Chem. 256, 7035-7041 (1981).
Throm. Res. 21, 65-71 (1981).
Biochim., Biophys. Acta 569, 177-183 (1979).
Wang and Smith [Anal. Biochem. 63, 414-417 (1975].
The Proteins (Neurath, H. and Hill, R. L., eds.), vol. 1, pp. 179-223, Academic Press, London (1975).
Biochem. J. 159, 545-553 (1976).
Biochem. J. 209, 837-646 (1983).
Haemostasis 5, 218-230, (1976).
Biochem. J. 225, 149-158, (1985).

Primary Examiner—Delbert R. Phillips
Assistant Examiner—Christina Chan
Attorney, Agent, or Firm—Brumbaugh, Graves, Donohue & Raymond

[57] ABSTRACT

The invention relates to Tetranectin, a new protein isolated from blood. Its structure comprises four polypeptide chains having the formula shown in the attached drawing.

Tetranectin plays a role in the hemostatic system and, therefore, may be used as an agent for regulation of hemostasis.

Further, the invention relates to a process for preparing Tetranectin in which Tetranectin is isolated e.g. from blood or blood fractions, cells or genetically engineered organisms.

Finally the invention relates to antiserum or antibodies against Tetranectin, to immunological detection and assay methods wherein said antiserum or antibodies are used as immunological reagent, and to pharmaceutical compositions containing Tetranectin or antibodies against Tetranectin.

6 Claims, 1 Drawing Sheet

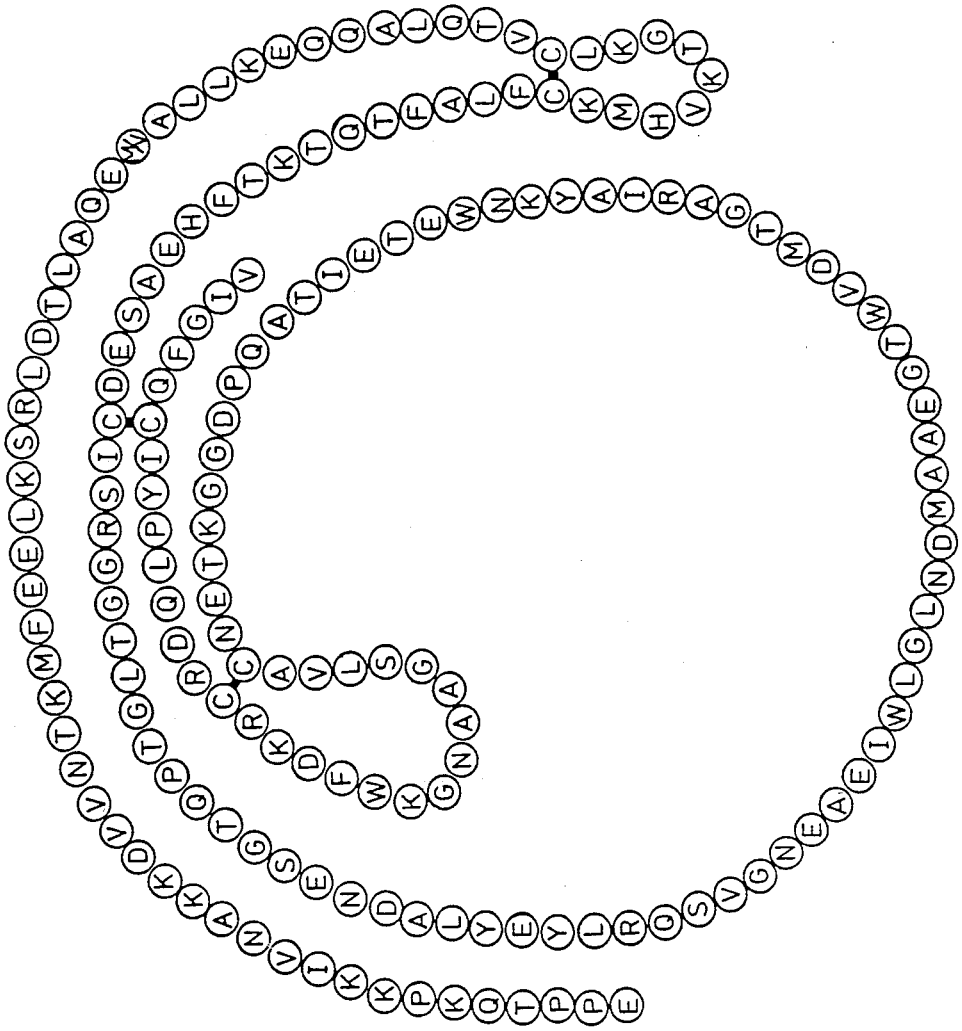

PROTEIN ISOLATED FROM BLOOD, PROCESS FOR PREPARING SAID PROTEIN, AANTIBODIES AGAINST SAID NEW PROTEIN, AND PHARMACEUTICAL COMPOSITIONS CONTAINING SAID PROTEIN OR SAID ANTIBODIES

The present invention relates to a new protein which has been isolated from human blood and is also present in blood of other mammals, such as bovine blood. This new protein has been found to bind specifically to kringle 4 of plasminogen, and has been called Tetranectin.

It was known that sodium dodecyl sulphate-polyacrylamide gel electrophoresis (SDS-PAGE) of $\alpha_2$-antiplasmin purified by affinity chromatography on plasminogen-Sepharose shows an additional weak band of a product having an apparent molecular mass of about 17,000 daltons. (Eur. J. Biochem. 120, 105-112 (1981)). The protein was considered to be a contaminant of the $\alpha_2$-antiplasmin preparation.

It was found that this protein of molecular mass 17,000 binds specifically to kringle 4 of plasminogen and not to kringle 1-3 or to miniplasminogen. The protein of molecular mass 17,000 was found to be an SDS dissociation product of a protein having a molecular mass of 68,000. The latter protein is the protein according to the invention, Tetranectin, which is described hereinafter in more detail.

The conversion of fibrinogen to fibrin is an important biological process. Fibrin formation is crucial in hemostasis, but it is also an important aspect of other biological processes, e.g., in inflammatory and misalignment diseases and in tissue repair. The degradation of fibrin deposits in the organism is catalyzed by the serine proteinase plasmin, and plasmin is formed from plasminogen under the influence of activators. This fibrin degradation is known to be controlled by these plasminogen activators, by plasmin inhibitors, and by activator inhibitors.

The most important inhibitory protein controlling the plasmin mediated fibrinolysis is $\alpha_2$-plasmin inhibitor ($\alpha_2 PI$). The observation that $\alpha_2$-$PI$ binds reversibly to the zymoen plasminogen has led to a simplified procedure for its purification. The inhibitor binds to plasminogen kringle 1-3 and can be disassociated from it by lysine. Thus $\alpha_2$-PI may be purified by affinity chromatography either on plasminogen-Sepharose or on kringle 1+2+3-Sepharose. However, recent studies suggest that it is not possible to purify all the $\alpha_2$-PI present in human plasma by this procedure. A fraction of circulating $\alpha_2$-PI is unable to form reversible complexes with plasminogen, whereas it still retains its inhibitory potential towards the active site of plasmin.

Thus two types of $\alpha_2$-PI, a plasminogen binding (PB$\alpha_2$-PI) and a non plasminogen binding form (NPB$\alpha_2$-PI) are present in human plasma. A preparation of PB$\alpha_2$PI purified by affinity chromatography on plasminogen-Sepharose spontaneously converts to NPB$\alpha_2$PI. The conversion is accompanied by the release of a peptide of molecular mass 2,000. In an attempt to identify a possible proteolytic enzyme in the PB$\alpha_2$PI preparation, responsible for this conversion, a contaminating protein has been identified, which protein is absent in preparations of $\alpha_2$-PI purified by affinity chromatography on kringle 1+2+3-Sepharose instead of plasminogen-Sepharose.

BRIEF DESCRIPTION OF THE FIGURE

The FIGURE shows the amino acid sequence of one of the polypeptide chains of tetranectin.

DETAILED DESCRIPTION OF THE INVENTION

The properties of Tetranectin will now be discussed in more detail.

Human plasminogen contains five homologous triple-loop, three disulphide bridge kringle structures in the N-terminal part of the molecule. Limited proteolysis of plasminogen with pancreatic elastase results in cleavage of kringle 1-3 and kringle 4 fragments from plasminogen. Such kringle structures which are also present in prothrombin, urokinase, tissue plasminogen activator and fibronectin are supposed to be involved in binding of ligands essential for the regulation of the biological function of these proteins. Purified plasminogen kringle 1-3 cleaved from plasminogen by elastase has been found to bind to fibrin, PB$\alpha_2$PI and histidine-rich glycoprotein. All of the resulting complexes dissociate in the presence of lysine. Tetranectin binds to the kringle 4 part of the plasminogen molecule, but not to the first three kringle structures in plasminogen or to miniplasminogen. Thus it seems to be the first compound described which binds specifically to kringle 4, without any ability to bind to kringle 1-3. Histidine-rich glycoprotein and $\alpha_2$PI which bind to kringle 1-3 do not bind to kringle 4.

The results suggest that although the first four kringles of plasminogen all bind lysine they have different ligand specifity. Tetranectin present as a contaminant in $\alpha_2$PI preparations cannot be removed therefrom by gel filtration. This is easily explained by the gel filtration experiments on Ultrogel ACA 34 to be described later. The estimated molecular mass of 68,000 for Tetranectin is very close to that of $\alpha_2$PI (67,000) and this explains why it was impossible to separate the two proteins by gel filtration. The results indicate that Tetranectin is a tetramer, which dissociates in SDS (1%) and in guanidine-hydrochloride 6 M.

The purified Tetranectin binds to $Ca^{++}$ and heparin.

Histidine-rich glycoprotein, which specifically binds to kringle 1-3 of plasminogen, bonds also to heparin. This binding is $Ca^{++}$ dependent and can be abolished by EDTA. There is no indication for such $Ca^{++}$ dependent interaction between kringle 4 and Tetranectin. The high NaCl concentration needed to elute Tetranectin from the heparin column, compared to the isoelectric point of the protein and experimental conditions (pH 7.4) in the heparin column, might indicate that the binding of Tetranectin to heparin might involve a specific heparin binding site in the molecule, as in antithrombin III.

The presence of $Ca^{++}$, EDTA or heparin seems to affect not only the net charge of the protein, but also its antigenicity. The very small precipitate obtained by electroimmunoassay in the presence of $Ca^{++}$ compared to results obtained in the presence of EDTA might indicate gross conformational changes in the molecule. For that reason quantitative electroimmunoassay of plasma or serum is impossible when performed in the absence of $Ca^{++}$. Quantification is in fact facilitated by the presence of EDTA. The influence of $Ca^{++}$ and EDTA on the electroimmunoassay with plasma or serum has nothing to do with binding to other components in plasma and serum. Identical results are obtained when purified Tetranectin is applied. The tetrameric form of the protein is not a result of Ca++ liganding, since the elution profile of the protein in a gel filtration experiment does not depend on the presence of Ca++ or EDTA. Only strong detergents are capable of dissociating the tetramer into monomers. Also the presence of Ca++ is not needed for the binding of Tetranectin to K 4 or plasminogen.

The total structure of tetranectin has been elucidated. It comprises four polypeptide chains, the structure of which is shown in the attached drawing in which the individual amino acid residues are indicated by the following code:

A alanine
B aspartic acid
E glutamic acid
F phenylalanine
G glycine
H histidine
I isoleucine
K lysine
L leucine
M methionine
N asparagine
P proline
Q glutamine
R arginine
S serine
T threonine
V valine
W tryptophan
Y tyrosine.

The N-terminal amino acid sequence is N-glu-pro-pro-thr-gln. Each of the four peptide chains contains 181 amino acids with three disulfide bridges in each chain and none between the chains. The molecular mass of each chain is estimated to be 20200. The protein does not contain any carbohydrate. There has been found homology with human, rat and chicken asialo-glycoprotein receptor from the liver. This indicates that the protein belongs to the family of lectins and four that reason might be a soluble receptor protein. Lectins are proteins, often glycoproteins, which bind to carbohydrate structures. In agreement with this tetranectin binds to heparin and chondroitin sulphates A, B and C as evaluated by crossed immunoelectrophoresis. Also in agreement with the family of lectins, tetranectin binds divalent metal ions and forms a polymeric structure. Additionally, tetranectin, like lectins, might be a mitogen possibly for estrogen dependent cell proliferation. Fertile women receiving oral contraceptives have a highly significant reduction in plasma level of tetranectin as also is the case in late pregnancy.

Summarizing, the properties of the new protein according to the invention, which is called Tetranectin, are the following:

Tetranectin is a tetrameric protein comprising four peptide chains each having a molecular mass of about 17,000 in polyacrylamide electrophoresis in the presence of sodium dodecyl sulphate, and has a calculated molecular mass of about 20,200.

The apparent molecular mass of the tetramer, as determined by gel chromatography on Ultrogel ACA 34, is about 68,000; based on amino acid analysis the molecular mass is calculated to be about 80,800.

The N-terminal amino acid sequence is N-glu-pro-pro-thr-gln.

The tetramer does not contain $\gamma$-carboxyglutamic acid residues.

It does not absorb to aluminum hydroxide or barium sulphate, indicating that it is not a vitamin-K dependent protein.

Tetranectin does not contain sugar residues, and is not a glycoprotein, as appears from the absence of binding to Concanavaline A and the absence of colour reaction with PAS reagent.

Tetranectin binds bivalent cations, such as calcium, nickel, cobalt and manganese, and to a lesser extent, zinc and magnesium.

Tetranectin binds to heparin. Binding occurs not only in the absence but also in the presence of free calcium ions. Crossed immunoelectrophoresis of Tetranectin in whole plasma shows that the $\beta$-mobility of Tetranectin becomes $\alpha$-mobility in the presence of heparin. A sharp single peak appears, which suggests that binding is strong and specific. This is in contrast with the results with chondroitin sulphates showing very broad peaks, and suggesting weaker binding.

Fibronectin binds to fibrin. About 15–20% of the Tetranectin disappears from the liquid when plasma is clotted. Further, Tetranectin could be detected on the fibrin. Binding to fibrin is significant only when free calcium ions are present. Binding to fibrin is independent of the activity of clotting factor XIII and cannot be influenced by EACA or by change of t-PA concentration. The binding to fibrin is proportional to the plasma level of tetranectin.

The isoelectric point of Tetranectin as determined by isoelectric focusing, is 5.8 in the absence of free calcium ions, and 7.8 in the presence thereof.

The electrophoretic mobility of Tetranectin in 1% agarose and pH 8.6 is the same as that of plasma $\beta$-2-globulins in the presence of calcium ions, and is the same as that of plasma $\alpha$-globulins in the absence of calcium ions. In the presence of heparin the mobility is the same as that of the $\alpha$-globulins in both cases.

The invention relates to Tetranectin having the above-mentioned properties. It also relates to method for preparing Tetranectin. In the first place, Tetranectin may be obtained from mammalian, such as human or bovine blood or blood fractions by means of usual protein purification techniques adapted to one or more of the properties of the protein.

A practical source of Tetranectin is human blood plasma, but Cohn's fraction III and cryoprecipitate depleated plasma are also suitable. It is also possible to isolate the protein from blood platelets. The occurrence of tetranectin in platelets and tissue sections of liver, breast and uterus indicate amongst others these tissues or precursor cells as sources for RNA for recombinant DNA techniques.

The invention includes Tetranectin produced by cell cultures or by micro-organisms or other hosts modified by recombinant DNA techniques.

Purification of Tetranectin can be effected by affinity chromatography on a column with coupled kringle 4 of plasminogen, on an antiTetranectin antibody column or on a heparin column. When impure antiplasmin is used as a source of Tetranectin, the kringle 4 column can be used successfully, but the antiplasmin may also be removed by adsorption to a kringle 1–3 column, and isolation of Tetranectin from the elute passing through the column.

In the same way, bovine Tetranectin may be isolated from e.g. bovine plasma by using the kringle 4 column.

Further isolation and purification methods are illustrated in the Examples.

The invention also relates to antisera and antibodies against Tetranectin. Antiserum may be prepared by immunizing an animal with Tetranectin, and isolating the serum. A monospecific antiserum has been obtained from immunized rabbits. The antiserum showed a single peak in crossed immunoelectrophoresis. A hybridoma cell line producing monoclonal antibodies against Tetranectin has been constructed as well.

The bovine Tetranectin cross-reacts with antisera against human Tetranectin.

Further the invention relates to detection and assay methods in which antibodies against Tetranectin are used. Any of the known immunological methods may be applied. For example, the electrophoretic method of Laurell or a sandwich ELISA technique may be used for quantitative assay of Tetranectin. The method should be carried out in the absence of free calcium ions. Any free calcium ions present may be complexed by addition of chelating agents, such as EDTA.

Tetranectin is present in human plasma in an average concentration of 0.2 $\mu$mol/l (15 mg/l). This average (100%) has been determined in normal healthy volunteers. Tetranectin concentration does not change during the day (0900 to 1500 hours). In 20 men 103±20% (standard deviation) and in 38 women 111±13% of the average concentration was found, the lowest value being 71%, and the highest value being 171%.

In patients with non-acute liver cirrhosis, plasma levels of tetranectin were significantly reduced to 83±28 (SD)% (n=28) with a lowest level of 26% in the studied group. This suggests the liver as site of synthesis, in agreement with immunohistochemical studies. The immunohistochemical method used was an indirect immunoperoxidase technique on formaldehyde fixed and trypsin treated tissue. The antibody used was rabbit antihuman tetranectin, affinity purified on a tetranectin-column. The antigen-antibody complex was detected by swine antirabbit IgG conjugated with peroxidase. The substrate for peroxidase was 3-amino-9-ethylcarbazole in dimethylformamide together with hydrogen peroxide. The control staining with the IgG fraction which did not adsorb to the tetranectin column was consistently negative. By the above method tetranectin was detected in tissue of the liver (hepatocytes), the endometrium of the uterus and in the ducts of glandular tissue (not in the vessels or connective tissues) of normal breast and breast carcinoma. Results were negative in the kidney, spleen, gastro-intentinal tract, prostate, skin, glandular thyroid, heart and the lung.

In triton extracts of pelleted, washed blood platelets, 23±8% (standard deviation) (n=3) (1% with respect to normal plasma) of Tetranectin was found. After treatment with thrombin 9±0,6% (n=3) was left, indicating that thrombin generated in the clotting process can release Tetranectin from platelets. This means that during clotting platelets are capable to add about 15% of additional Tetranectin to the blood concentration.

Tetranectin is an adhesion factor binding to various components of the hemostatic mechanism, such as plasminogen, fibrin, heparin, platelets. Most probably, the primary binding is with kringle 4 of plasminogen.

Tetranectin stimulates and controls the plasminogen activation resulting in a higher rate of clot lysis or fibrinolysis, especially in the presence of blood platelets and in the presence of a complex fibrin clot from blood.

Secondly, Tetranectin stimulates and controls the plasminogen activation in the absence of fibrin, but in the presence of a cofactor, such as polylysine. This fibrin independent plasminogen activation may play a role in tissue growth and repair processes.

It was found that binding of Tetranectin to fibrin is not disturbed by excess heparin, and that binding to fibrin is not influenced by binding to plasminogen. Addition of plasminogen to a fibrinTetranectin complex had no effect, and addition of EACA, which breaks the plasminogen-Tetranectin bond, has no effect on the Tetranectin-fibrin complex.

Binding to heparin is not or not easily replaced with binding to plasminogen. In crossed immunoelectrophoresis in calcium containing medium plasminogen cannot cancel the heparin induced mobility change.

These results suggest that the tetrameric structure of Tetranectin would allow several simultaneous bonds to heparin, fibrin, and plasminogen to different sub-units. This would explain the adhesive function of Tetranectin.

Tetranectin plasma concentration appears to decrease significantly after various traumas, such as surgical operations, myocardial infarct and cancer. This behaviour resembles that of a negative acute phase reactant. The effect is relatively long lasting, and the plasma concentration may be an indicator for presence or recovery from trauma. In a group of 24 patients which underwent major abdominal surgery preoperative tetranectin levels were reduced and reduced further postoperatively. In the nine patients which developed postoperative deep vein thrombosis the tetranectin concentration at the first post-operative day was significantly lower (mean 48%) than in the 14 without thrombosis (mean 60%) (p 0.05).

In view of its stimulating activity on clot lysis, Tetranectin may be used as an agent for regulation of hemostasis. Increasing or reducing Tetranectin blood levels by administration of Tetranectine or of Tetranectine inhibitors, respectively, such as anti-Tetranectine antibodies, also may be of value in the treatment of malignant neoplasia.

Therefore, the invention also relates to pharmaceutical compositions containing Tetranectin as an active principle. Further, the invention relates to pharmaceutical compositions containing antibodies against Tetranectin.

The following Examples serve to illustrate the invention. The materials and methods used in the Examples are as follows:

Buffers and chemicals.

Tris: 0.05 M Tris/HCl 0.10 M NaCl adjusted to pH 7.70 (20° C.) with NaOH, I=0.15 mol/l. Sodium phosphate 0.04 pH 7.4. Ammonium sulphate was from Merck (Darmstadt, German Federal Republic).

Tranexamic acid and D-Val-Leu-Lys-Nan (S 2251) were from Kabi (Stockholm, Sweden). Lyophilized ammonium heparin (150,000 U/mg) was from Leo Pharmaceuticals, Copenhagen, Denmark).

Agarose A 37 (Indubiose®, EEO=% 0.17) was from L'Industries Biologique (France). Ultrogel ACA 34 and 44 were from LKB (Sweden). Sepharose 4B Cyanogen bromide activated, heparin-Sepharose en DEAESepharose CL-6B were from Pharmacia (Sweden).

Proteins.

Fresh or outdated plasma was obtained from donor blood (stabilized by 0.13 vol of a solution containing sodium citrate, 0.073 M, citric acid, 0,038 M; and glucose, 0.124 M.

Plasminogen was prepared by affinity chromatography on lysineSepharose as described in Biochim. Biophys. Acta 668, 377–387 (1981). Glu$_1$-plasminogen and Lys$_{77}$-plasminogen were prepared as described in the same article.

Plasminogen-Sepharose was prepared by coupling 30 μM plasminogen to 60 g CNBr-activated Sepharose 4 B as described in Christensen, U. and Clemmensen, I. (1978). Biochem. J. 175, 635–641.

Preparation and separation of kringle 1+2+3 (K 1+2+3) and kringle 4 (K 4) from the N-terminal part of plasminogen was performed by digestion of plasminogen by pancreatic elastase as described in Progress in Chemical Fibrinolysis and Thrombolysis (Davidson, J. F., Rowan, R. M., Samana, M.M. and Desnoyers, P.C. eds.) vol. 3, pp 191–209, Raven Press, New York (1978).

Ten μM K 1+2+3 and 8 μM K 4 was coupled to 20 and 15 g activated Sepharose, respectively.

All affinity chromatography experiments were performed in sodium phophate buffer 0.04 M pH 7.4, and the elution was performed with tranexamic acid 1 mM.

Human fibrinogen was from IMCO (Sweden). *Bovine thrombin* was from Novo (Denmark). Urokinase was the reagent preparation from Leo Pharmaceuticals (Denmark). *Human melanoma cell plasminogen activator* was purified as described in J. Biol. Chem. 256, 7035–7041 (1981). Immunoglobulin against α$_2$plasmin inhibitor, plasminogen, fibrinogen, and IgG were all from Dakopatt (Denmark).

Determination of protein concentrations.

The concentration of plasminogen K 1+2+3, K 4 and α$_2$PI was determined spectrophotometrically [Thromb. Res. 21, 65–71 (1981) and Progress in Chemical Fibrinolysis and Thrombolysis (Davidson, J. F., Rowan, R. M., Samana, M. M. and Desnoyers, P. C. eds.) vol. 3, pp 191–209, Raven Press, New York (1978)]. The concentration of urokinase 1 mol=5.6×10$^{12}$ Ploug units [Biochim., Biophys. Acta 569, 177–183 (1979)] was used to calculate the molar concentration of melanoma cell activator using its mass concentration and molecular mass=70,000 [J. Biol. Chem. 256, 7035–7041 (1981)].

Concentration of proteins were also determined by the method described by Lowry et al [J. Biol. Chem. 193, 265–275 (1951)] as modified by Wang and Smith [Anal. Biochem. 63, 414–417 (1975)], using albumin as reference and by electroimmuno assay as described by Laurell [Scand. J. Clin. Lab. Invest. 29, Suppl. 124, 21–37, (1972)].

Polyacrylamide gel electrophoresis in SDS (SDS-PAGE) was performed as described in The Proteins (Neurath, H. and Hill, R. L., eds.), Vol 1 pp 179–223, Academic Press, London (1975). Molecular mass determinations were carried out using reference proteins from Pharmacia (LMW Calibration Kit proteins).

Ultrafiltration of proteins was performed as described in Biochem. J. 159, 545–553 (1976).

Purification of β$_2$PI was performed by the use of plasma or cryoprecipitate depleted plasma by two different methods as described in Eur. J. Biochem. 120, 105–112, (1981).

Briefly the method comprises the following steps: Removal of plasminogen by affinity chromatography on lysine-Sepharose fractionation by (NH$_4$)$_2$SO$_4$ (0.8–2.7M), affinity chromatography, on plasminogen-Sepharose (Method A) or K 1+2+3-Sepharose (Method B), ion exchange chromatography on DEAE CL 6B at pH 7.4 and gel filtration on Ultrogel ACA 34.

Gel Filtration of PBα$_2$PI purified by method A on Sephadex G75 superfine.

This was performed in a column (5.3 cm$^2$×90 cm) equilibrated and eluted with Tris-HCl 0.05 M, NaCl 0.1 M pH 7.4 with and without guanidine hydrochloride 6 M. The sample applied contained 30 nmol PBβ$_2$PI purified by method A dissolved in the same buffer. After elution the protein was estimated by measurement of the absorbance at 280 nm. The eluted protein peaks were pooled and concentrated by ultrafiltration (Amicon, USA) and applied to SDS-PAGE (sodium dodecyl sulphate polyacrylamide gel electrophoresis).

Gel filtration on Ultrogel ACA 34. This was performed in a column (5.3 cm$^2$×90 cm) equilibrated and packed with Tris buffer with or without CaCl$_2$ 2 mM or EDTA 2 mM. The column was calibrated by the use of different marker proteins.

Isoelectric focusing was performed in a Multiphor system 2117 (LKB, Products AB, Bromma, Sweden) using a constant voltage power supply ISCO model 490, polyacrylamide gradient gels (pH 3.5–9.5), anode and cathode-electrode solutions, sample application pieces and electrode focusing (Instrumentation Specialties Company, Lincoln Neb., USA). Strips were from LKB Products. Preelectrophoresis was run at 1,000 V for 30 min. and the electrophoresis was run after application of 0.6 nmol K-4 binding protein at 1,000 V for 2.5 hours. Calibration of pH gradient was performed using Isoelectric Focusing Calibration Ket (pH 3–10) from Pharmacia.

Affinity chromatography on heparin-Sepharose.

This was performed with heparin-Sepharose (Pharmacia) packed in a column (1,76 m$^2$×8 cm) and equilibrated with Tris buffer prepared from water passed through chelex 100 (200–400 mesh, from Biorad). Affinity chromatography in the absence of Ca$^{++}$ (Experiment A) was performed with a sample (30 nmol of purified K-4 binding protein in 10 ml trisbuffer) which was dialysed overnight against 200 vol trisbuffer, 5 mmol EDTA and again against 200 vol trisbuffer. The column was washed with 20 ml trisbuffer and the protein eluted with a linear salt gradient formed by mixing 300 ml trisbuffer and 300 ml trisbuffer containing 1,0 M NaCl.

Affinity chromatography in the presence of Ca$^{++}$ (Experiment B) was performed with a sample dialysed against trisbuffer, and 5 mM CaCl$_2$. The column was washed and the protein eluted as in Experiment A, but the buffers contained 5 mM CaCl$_2$, instead of EDTA.

Adsorption of γ-carboxyglutamic acid containing plasma proteins to barium citrate. This was performed as described in Biochem. J. 209, 837–646 (1983). The supernatant after adsorption and the proteins eluted by EDTA were subjected to quantitative electroimmunoassay with antibody raised against the purified K-4 binding protein.

Fibrin clot lysis assay. This was performed as described by the use of urokinase and melanoma tissue activator [Haemostasis 5, 218–230, (1976)].

Plasminogen activation catalyzed by melanoma cell tissue activator in the presence of poly-D-lysine.

This was performed by use of the specific chromogenic peptide substrate for plasmin, Val-Leu-Lys-Nan, in the presence of poly-D-lysine as described [Biochem.

J. 225, 149–158, (1985)], in the absence and in the presence of increasing amounts of the purified protein.

EXAMPLE I Purification of PBα2PI.

The inhibitor preparation purified by both method A and B both exhibited a molecular mass of 67,000. In the PBα2PI preparation purified by method A an additional protein band with a molecular mass of 17,000 (by SDS-PAGE) was found, whereas it was absent in the inhibitor preparation purified by method B. Attempts to remove the contaminating protein by gel filtration in the absence of denaturing agents was unsuccessful. The protein was eluted together with PBα2P when applied to gel filtration on Sephadex G 75 superfine and eluted I with trisbuffer, whereas the two proteins appear as separate peaks in an identical gel filtration experiment in the presence of guanidine hydrochloride 6 M.

EXAMPLE II Affinity chromatography on K 4- and K 1+2+3-Sepharose of an inhibitor preparation by method A.

A. The ligand used for affinity purification of α2PI by method B, differs from that used in method A by the lack of the miniplasminogen and kringle 4 parts of plasminogen. This suggests that the contaminating protein present in the inhibitor preparation by method A, was adsorbed to the kringle 4 part of the plasminogen ligand. Therefore, an experiment was set up, in which a preparation containing 50 nmol of inhibitor obtained by method A was applied to affinity chromatography on K 4-Sepharose. The inhibitor appeared in the void volume, whereas the copurified protein was retained and subsequently eluted from the column with tranexamic acid 1 mmol/l. The eluate contained the copurified component showing a molecular mass of 17,000 by SDS-PAGE in almost pure form. The copurified protein did not bind to a column with coupled miniplasminogen.

B. Application of the inhibitor preparation obtained by method A to a K 1+2+3-Sepharose column resulted in the appearance of the protein of molecular mass 17,000 in the void volume, whereas the inhibitor was retained by the column and could be eluted with tranexamic acid 1 mmol/l.

EXAMPLE III Gel Filtration of Ultrogel ACA 34 of the K 4-binding protein.

When the preparation of K 4-binding protein obtained according to Example II A was applied to a calibrated Ultrogel ACA 34 column, the protein was eluted just in front of albumin suggesting a molecular mass of about 70,000 (five different experiments). This is in accordance with the Sephadex G 75 gel filtration experiments in the absence of guanidine hydrochloride, but is is apparently in conflict with the molecular mass of about 17,000 obtained by SDS-PAGE. This descrepancy can be explained if it is assumed that K 4-binding protein exists as an oligomeric (tetrameric) protein, which is dissociated by SDS. The gel filtration experiments performed in the presence of guanidine hydrochloride also support this assumption.

Plasma (5 ml) or serum was also applied to the calibrated Ultrogel column, and the elution profile monitored by electroimmuno assay of α2PI and K 4-binding protein. In accordance with the results obtained with the preparation of α2PI containing co-purified K 4-binding protein the two proteins are both eluted as proteins with a molecular mass of about 70,000.

EXAMPLE IV Purification of the K 4-binding protein from plasma.

A method for the purification of the K-binding protein in plasma was developed. The protein was found in the supernatant after barium citrate precipitation. Plasminogen was removed from 1 l plasma by affinity chromatography on lysine-Sepharose and the optimum conditions for $(NH_4)_2SO_2$ precipitation of the protein from plasminogen depleted plasma were determined and found to be similar to those used in α2PI purification (0.8 M–2.7 M). The precipitate obtained after addition of $(NH_4)SO_4$ (2.7 M) was dissolved in sodium phosphate buffer 0.04 M, pH 7.4 and dialysed overnight against the same buffer. The dialysed plasma was applied to a column (5.2 cm$^2$ × 10 cm) packed with K 4-Sepharose. The column was percolated with phosphate buffer until absorbance at 280 nm was below 0.050. The protein was eluted with tranexamic acid 1 mM in the same buffer. Elution of the protein was followed by means of electroimmuno assay, and the fractions were pooled and applied to a DEAE CL6 B-Sepharose column (5.2 cm$^2$ × 10 cm) equilibrated with sodium phosphate buffer 0.04 M pH 7.4. Elution was performed with a linear gradient of 300 ml equilibration buffer and 300 ml equilibration buffer with NaCl 0.3 M added. The eluate fraction containing the K 4-binding protein was concentrated to 5 ml and applied to a column (5.2 cm$^2$ × 90 cm) packed with Ultrogel ACA 34 in trisbuffer. Elution of the protein was again followed by electroimmuno assay, and the fractions were pooled and concentrated to 5 ml. SDS-PAGE of the purified protein revealed only one band with a molecular mass of 17,000. Based on measurements of the absorbance at 280 nm and the protein concentration determined by the Lowry method an absorbance coefficient of $E^{1\%}_{280\ nm} = 12,5$ was obtained.

A preparation of purified protein (0.2 g/l) was used as a standard in quantitative electroimmuno assay to determine the concentration in plasma and the yield of the protein in the different fractionation steps. The concentration in plasma was estimated to be about 15 mg/l or 0.2 mol/l.

EXAMPLE V

Crossed immunoelectrophoresis.

In a crossed immunoelectrophoresis of plasma (or serum) at pH 8.6 the K 4-binding protein was found to posses a net charge giving rise to a mobility similar to that of β-globulins. The purified K 4-binding protein was also found in the β-region. The electrophoretic mobility at pH 8.6 of the purified K 4-binding protein was highly influenced by EDTA 2 mmol/l in the first dimension of the electrophoresis. The mobility of the protein changed from β-globulin to inter-α-globulin mobility. Also the presence of Ca$^{++}$ (2 mmol/l) in the first dimension of the electrophoresis changed the electrophoretic mobility. In addition, the shape of the immunoprecipitates appeared to be highly influenced bij Ca$^{++}$. The presence of Ca$^{++}$ resulted in very small precipitate peaks, while the presence of EDTA resulted in high precipitate peaks. The presence of heparin (5 × 10' units/l in the gel and the gel buffer) also results in increased electrophoretic mobility of the K 4-binding protein. The electrophoretic mobility and the shape of the precipitate were nearly identical with the results obtained when EDTA was present during the electrophoresis. A similar influence of Ca$^{++}$, EDTA and heparin on the electrophoretic mobility of the K 4-binding protein was also seen when plasma was employed.

EXAMPLE VI

Electroimmuno assay according to Laurell.

The rocket immunoelectrophoresis was also influenced by the absence or presence of Ca++, EDTA and heparin.

The presence of Ca++ (2 mM) in the gel and the buffer nearly prevents the formation of immunoprecipitate when plasma and serum were applied, whereas application of EDTA 2 mM to gel and buffer results in normal rockets.

EXAMPLE VII

Association to heparin-Sepharose.

The K 4-binding protein was retained by heparin-Sepharose both in the absence as well as in the presence of Ca++. Addition of EDTA 5 mM to experiment B (in the presence of Ca++) did not release the K 4-binding protein from the heparin column, indicating that EDTA and heparin did not compete for Ca++ in the K 4-binding protein. This might indicate that the heparin binding to the K-binding protein does not involve Ca++. In both experiments was the K 4-binding protein released from the column by addition of NaCl between 0.3 to 0.45 M.

EXAMPLE VIII

Isoelectric focusing and N-terminal amino acids.

The isoelectric point by isoelectric focusing was found to be 5.8. The first 5 N-terminal amino acids were found to be N-glu-pro-pro-thr-gln.

EXAMPLE IX

Fibrin clot lysis assay.

Addition of various amounts of K 4-binding protein between 0.1 and 2.0 µmol/l (final concentration) to a fibrin clot system with purified fibrin which also contains plasminogen and urokinase, did not affect the clot dissolution time compared to dissolution time obtained in the absence of K 4-binding protein. The same applies to similar experience with melanoma cell plasminogen activator (t-PA).

In contrast with this, lysis of whole blood enriched with melanoma cell plasminogen activator and with thrombin, was accelerated by addition of the purified K-4 binding protein (Tetranectin), and inhibited by addition of purified immunoglobulins obtained from antiserum against Tetranectin induced in rabbits.

EXAMPLE X

Potentation of poly-D-lysine stimulated plasminogen activation.

This experiment shows the effect of K 4-binding protein on t-Pa catalysed $Glu_1$-plasminogen activation in the presence of poly-D-lysine. Addition of this protein resulted in an augmentation in the rate of plasmin generation relative to the rate obtained in the presence of only poly-D-lysine. This rate is again much higher than the rate obtained in the absence of poly-D-lysine. The augmentation induced by K 4-binding protein followed a saturation curve with half-maximal effect at about 0.25 µM.

We claim:

1. A substantially purified protein called Tetranectin showing at least the following properties:
   a. it has an apparent molecular mass of about 68,000 as determined by gel chromatography on Ultrogel ACA 34, and of about 80,800 calculated from the amino acid composition,
   b. in the presence of sodium dodecyl sulphate the protein dissociates into a protein sub-unit having an apparent molecular mass of about 17,000 by SDS-PAGE, or of about 20,200 calculated from the amino acid composition,
   c. the N-terminal sequence of the protein is N-glu-pro-pro-thr-gln,
   d. the protein binds specifically to kringle 4 of plasminogen,
   e. the protein does not contain $\alpha$-carboxyglutamic acid residues,
   f. the protein does not contain sugar residues and is not a glycoprotein,
   g. the protein binds bivalent cations,
   h. the protein binds to heparin and, in the presence of calcium ions, to fibrin.

2. A substantially purified protein according to claim 1, having an electrophoretic mobility in the presence of calcium ions comparable to beta-2-globulins and in the absence of calcium ions comparable to alpha-globulins.

3. A substantially purified protein according to claim 2, having an isoelectric point of 5.8 in the absence of free calcium ions, and 7.8 in the presence of free calcium ions.

4. A substantially purified protein according to claim 3, having an absorbence coefficient, $E1\%280$, of about 12.5.

5. A pharmaceutical preparation comprising a pharmaceutically acceptable carrier and an effective hemostatic regulating amount of tetranectin according to anyone of claim 1 and 2-4.

6. A method of regulating hemostasis in mammals including man comprising administering to a mammal in need of hemostatic regulation an amount of tetranectin according to anyone of claim 2 and 23-25 such that clot lysis in the mammal is controlled.

* * * * *

UNITED STATES PATENT AND TRADEMARK OFFICE
CERTIFICATE OF CORRECTION

PATENT NO. : 4,853,220

DATED : August 1, 1989

INVENTOR(S) : Clemmensen et al.

It is certified that error appears in the above-identified patent and that said Letters Patent is hereby corrected as shown below:

TITLE PAGE: 3rd line of Item 54, AND col. 1, line 2, "AANTIBODIES" should read --ANTIBODIES--;
TITLE PAGE: Item 73, "Toegerastnatuurwete Nschappelijk" should read --Toegepast-Natuurwetenschappelijk--;
First page, Item 56, line 17, "Clemmense" should read --Clemmensen--;
Col. 1, line 34, "misalignment" should read --malignant--;
Col. 1, line 45, "zymoen" should read --zymogen--;
Col. 3, line 42, "four" should read --for--;
Col. 4, line 3, "absorb" should read --adsorb--;
Col. 4, line 41, "method" should read --methods--;
Col. 4, line 49, "depleated" should read --depleted--;
Col. 4, line 65, "elute" should read --eluate--;
Col. 6, line 39, "Tetranectine" (both instances) should read --Tetranectin--;
Col. 6, line 54, "0.04" should read --0.04M--;
Col. 7, line 60, "$\beta_2 PI$" should read --$\alpha_2 PI$--;
Col. 8, line 9, "PB$\beta_2$PI" should read --PB$\alpha_2$PI--;
Col. 9, line 13, "PB$\alpha_2$P" should read --PB$\alpha_2$PI--;
Col. 9, line 45, "of" should read --on--;
Col. 9, line 55, "is is" should read --it is--;
Col. 9, lines 56-57, "descrepancy" should read --discrepancy--;
Col. 10, line 59, "bij" should read --by--
Col. 11, line 43, "experience" should read --experiments--;
Col. 12, line 27, "$\alpha$-carboxyglutamic" should read --$\gamma$-carboxyglutamic--;

UNITED STATES PATENT AND TRADEMARK OFFICE
CERTIFICATE OF CORRECTION

PATENT NO. : 4,853,220

DATED : August 1, 1989

INVENTOR(S) : Clemmensent et al.

It is certified that error appears in the above-identified patent and that said Letters Patent is hereby corrected as shown below:

Col. 12, line 48, "anyone of claim" should read --any one of claims--;
Col. 12, line 52, "anyone of claim 2 and 23-25" should read --any one of claims 1-4--.

Signed and Sealed this

Seventh Day of July, 1992

Attest:

DOUGLAS B. COMER

Attesting Officer

Acting Commissioner of Patents and Trademarks